US012626783B2

(12) United States Patent
Plagnol et al.

(10) Patent No.: US 12,626,783 B2
(45) Date of Patent: May 12, 2026

(54) COMPUTER-IMPLEMENTED METHOD AND APPARATUS FOR ANALYSING GENETIC DATA

(71) Applicant: GENOMICS LIMITED, Oxford (GB)

(72) Inventors: Vincent Yann Marie Plagnol, Oxford (GB); Rachel Moore, Oxford (GB); Eva Maria Laura Krapohl, Oxford (GB); Christopher Charles Alan Spencer, Oxford (GB)

(73) Assignee: GENOMICS LIMITED, Oxford (GB)

( * ) Notice: Subject to any disclaimer, the term of this patent is extended or adjusted under 35 U.S.C. 154(b) by 1089 days.

(21) Appl. No.: 17/753,271

(22) PCT Filed: Aug. 28, 2020

(86) PCT No.: PCT/GB2020/052060
§ 371 (c)(1),
(2) Date: Feb. 25, 2022

(87) PCT Pub. No.: WO2021/038234
PCT Pub. Date: Mar. 4, 2021

(65) Prior Publication Data
US 2022/0367009 A1     Nov. 17, 2022

(30) Foreign Application Priority Data
Aug. 28, 2019    (GB) ..................................... 1912331

(51) Int. Cl.
*G16B 40/00*      (2019.01)
*C12Q 1/6883*     (2018.01)
*G16B 50/00*      (2019.01)

(52) U.S. Cl.
CPC ........... *G16B 40/00* (2019.02); *C12Q 1/6883* (2013.01); *G16B 50/00* (2019.02)

(58) Field of Classification Search
CPC ........ G16B 40/00; G16B 50/00; G16B 40/20; C12Q 1/6883
See application file for complete search history.

(56) References Cited

U.S. PATENT DOCUMENTS

2009/0307180 A1* 12/2009 Colby ................. C12Q 1/6886
                                                          706/54
2015/0066378 A1*  3/2015 Robison ................ G16B 20/00
                                                          702/19

(Continued)

FOREIGN PATENT DOCUMENTS

CN        1809644  A     7/2006
CN      109196590  A     1/2019

(Continued)

OTHER PUBLICATIONS

Kichaev G, Yang WY, Lindstrom S, Hormozdiari F, Eskin E, Price AL, Kraft P, Pasaniuc B. Integrating functional data to prioritize causal variants in statistical fine-mapping studies. PLoS Genet. Oct. 30, 2014;10(10):e1004722. doi: 10.1371/journal.pgen.1004722. PMID: 25357204; PMCID: PMC4214605. (Year: 2014).*

(Continued)

*Primary Examiner* — Sun M Li
(74) *Attorney, Agent, or Firm* — Kilpatrick Townsend & Stockton LLP

(57)                    ABSTRACT

The disclosure relates to analysing genetic data. In one arrangement, a method operates on input data comprising strengths of association between one or more phenotypes including a target phenotype and a plurality of genetic variants. A fine-mapping algorithm is applied to all or a subset of the input data to identify one or more independent phenotype-variant associations. A set of one or more fine-mapped variants is identified for each association. A fine-mapping predictive model is calculated on the basis of the input data and the set of fine-mapped variants. The effect on (Continued)

the target phenotype of the set of fine-mapped variants is subtracted from the input data to obtain residual association data. A machine learning algorithm is applied to the residual association data to identify further predictive correlations between the target phenotype and the plurality of genetic variants.

26 Claims, 6 Drawing Sheets

(56)  References Cited

U.S. PATENT DOCUMENTS

| | | | | |
|---|---|---|---|---|
| 2016/0085909 A1 * | 3/2016 | Reese | .................... | G16C 20/60 |
| | | | | 702/19 |
| 2016/0092631 A1 * | 3/2016 | Yandell | .................. | G16B 50/10 |
| | | | | 702/19 |
| 2017/0286594 A1 * | 10/2017 | Reid | ...................... | G16B 45/00 |
| 2019/0005192 A1 * | 1/2019 | Kermani | .............. | C12Q 1/6806 |
| 2019/0087534 A1 * | 3/2019 | Zhang | ..................... | G06F 17/16 |
| 2019/0311785 A1 * | 10/2019 | Torkamani | ............. | G16B 20/40 |

FOREIGN PATENT DOCUMENTS

| | | | | |
|---|---|---|---|---|
| CN | 109637582 A | 4/2019 | | |
| WO | WO-2015042496 A1 * | 3/2015 | ........... | B05B 7/0416 |
| WO | WO-2018051072 A1 * | 3/2018 | ............. | G16B 40/20 |
| WO | 2019166792 | 9/2019 | | |
| WO | WO-2021011990 A1 * | 1/2021 | ............. | G16B 20/40 |

OTHER PUBLICATIONS

Spain SL, Barrett JC. Strategies for fine-mapping complex traits. Hum Mol Genet. Oct. 15, 2015;24(R1):R111-9. doi: 10.1093/hmg/ddv260. Epub Jul. 8, 2015. PMID: 26157023; PMCID: PMC4572002. (Year: 2015).*

Pepke S, Ver Steeg G. Comprehensive discovery of subsample gene expression components by information explanation: therapeutic implications in cancer. BMC Med Genomics. Mar. 15, 2017;10(1):12. doi: 10.1186/s12920-017-0245-6. PMID: 28292312; PMCID: PMC5351169. (Year: 2017).*

Emmert-Streib F, Tripathi S, de Matos Simoes R. Harnessing the complexity of gene expression data from cancer: from single gene to structural pathway methods. Biol Direct. Dec. 10, 2012;7:44. doi: 10.1186/1745-6150-7-44. PMID: 23227854; PMCID: PMC3769148. (Year: 2012).*

Shepard SS, Meno S, Bahl J, Wilson MM, Barnes J, Neuhaus E. Viral deep sequencing needs an adaptive approach: IRMA, the iterative refinement meta-assembler. BMC Genomics. Sep. 5, 2016;17(1):708. doi: 10.1186/s12864-016-3030-6. Erratum in: BMC Genomics. Oct. 13, 2016;17(1):801.doi: 10.1186/s12864-016-3138- (Year: 2016).*

Spain SL, Barrett JC. Strategies for fine-mapping complex traits. Hum Mol Genet. Oct. 15, 2015;24(R1):R111-9. doi: 10.1093/hmg/ddv260. Epub Jul. 8, 2015. PMID: 26157023; PMCID: PMC4572002. (Year: 2015) (Year: 2015).*

Chinese Application No. 202080061338.1, Office Action mailed on Apr. 21, 2025, 11 pages (6 pages of original document and 5 pages of English Translation).

Pan, Two-stage Design and Analysis for Genome-wide Association Studies, Medical and Health Technology, Oct. 15, 2012, 106 pages.

Benner et al., FineMap: Efficient Variable Selection Using Summary Data from Genome-Wide Association Studies, Bioinformatics, vol. 32, No. 10, Jan. 14, 2016, pp. 1493-1501.

Chatterjee et al., Developing and Evaluating Polygenic Risk Prediction Models for Stratified Disease Prevention, Nature Reviews Genetics, vol. 17, No. 7, Jul. 2016, pp. 392-406.

Choi et al., A Guide to Performing Polygenic Risk Score Analyses, Nature Protocols, Sep. 14, 2018, 22 pages.

Lambert et al., Towards Clinical Utility of Polygenic Risk Scores, Human Molecular Genetics, vol. 28, No. R2, Nov. 21, 2019, pp. R133-R142.

International Application No. PCT/GB2019/050525, International Preliminary Report on Patentability mailed on Sep. 3, 2020, 15 pages.

International Application No. PCT/GB2019/050525, International Search Report and Written Opinion mailed on Jun. 6, 2019, 18 pages.

International Application No. PCT/GB2020/052060, International Preliminary Report on Patentability mailed on Mar. 10, 2022, 9 pages.

International Application No. PCT/GB2020/052060, International Search Report and Written Opinion mailed on Nov. 3, 2020, 9 pages.

Spain et al., Strategies for Fine-Mapping Complex Traits, Human Molecular Genetics, vol. 24, No. R1, Jul. 8, 2015, pp. R111-R119.

Vilhjalmsson, Modeling Linkage Disequilibrium Increases Accuracy of Polygenic Risk Scores, The American Journal of Human Genetics, vol. 97, Oct. 1, 2015, pp. 576-592.

Yang et al., Conditional and Joint Multiple-SNP Analysis of GWAS Summary Statistics Identifies Additional Variants Influencing Complex Traits, Nature Genetics, vol. 44, No. 4, Mar. 18, 2012, pp. 369-375.

Zhu et al., Bayesian Large-Scale Multiple Regression with Summary Statistics from Genome-wide Association Studies, The Annals of Applied Statistics, vol. 11, No. 3, Available Online at: https://projecteuclid.org/euclid.aoas/1507168840, Sep. 2017, pp. 1561-1592.

* cited by examiner

COMPUTER-IMPLEMENTED METHOD AND APPARATUS FOR ANALYSING GENETIC DATA

CROSS-REFERENCE TO RELATED APPLICATIONS

This application is a U.S. National Stage of International Application No. PCT/GB2020/052060, filed Aug. 28, 2020, which claims priority to Great Britain Application No. 1912331.4, filed Aug. 28, 2019, which are hereby incorporated by reference in their entireties for all purposes.

The invention relates to analysing genetic and phenotype data about an organism to obtain information about the organism, particularly in the context of enabling improved polygenic risk scores (PRSs) to be obtained for phenotypes of interest.

A PRS is a quantitative summary of the contribution of an organism's inherited DNA to the phenotypes that it may exhibit. A PRS may include all DNA variants relevant (either directly or indirectly) to a phenotype of interest or may use its component parts if these are more relevant to a particular aspect of an organism's biology (including cells, tissues, or other biological units, mechanisms or processes). A PRS can be used directly, or as part of a plurality of measurements or records about the organism, to infer aspects of its past, current, and future biology. In the context of improving human health and healthcare, PRSs have a range of practical uses, which include, but are not limited to: predicting the risk of developing a disease or phenotype, predicting age of onset of a phenotype, predicting disease severity, predicting disease subtype, predicting the response to treatment, selecting appropriate screening strategies for an individual, selecting appropriate medication interventions, and setting prior probabilities for other prediction algorithms. PRS may have direct use as a source of input in the application of artificial intelligence and machine learning approaches to making predictions or classifications from other high dimensional input data (for example imaging). They may be used to help train these algorithms, for example to identify predictive measurements based on non-genetic data. As well as having utility in making predictive statements about an individual, they can also be used to identify cohorts of individuals, included but not limited to the above applications, by calculating the PRS for a large number of individuals, and then grouping individuals on the basis of the PRSs. PRSs can also aid in the selection of individuals for clinical trials, for example to optimise trial design by recruiting individuals more likely to develop the relevant disease or phenotypes, thereby enhancing the assessment of the efficacy of a new treatment. PRSs carry information about the individuals they are calculated for, but also for their relatives (who share a fraction of their inherited DNA). Information about the impact of an individual's DNA on their phenotypes can derive from any relevant assessment of the potential impact of carrying any particular combination of DNA variants. In what follows we focus on the analysis of the recent wealth of information that derives from genetic association studies (GAS). These studies systematically assess the potential contribution of DNA variants to the genetic basis of a phenotype.

Since the mid-2000s, GAS (typically genome-wide association studies: GWAS, or association studies targeting single variants, or variants in a region of the genome, or GWAS restricted to a particular region of the genome) have been conducted on many thousands of (largely human) phenotypes, in millions of individuals, generating billions of potential links between genotypes and phenotypes. The resulting raw data is often then simplified to produce summary statistic data. GAS summary statistic data consists of, for each genetic variant (whether imputed or observed), the inferred effect size of the genetic variant on the phenotype of the GAS and the standard error of the inferred effect size. In other cases the individual level data, consisting of a full genetic profile of the individuals in a study and information about their phenotypes, may be available directly. However, individual level data is typically less widely available due to requirements on the privacy of an individual's data.

In what follows, we refer to a phenotype as being synonymous with a single study. However, it is quite often the case that data are available from multiple different studies on the same or similar phenotypes, or from a single cohort from which multiple different phenotypes are measured.

A PRS consists of the aggregation of the effects of a large number of genetic variants, typically each having small individual effects, to build an aggregate predictor for a trait of interest. Variants included in such a score can either be "causal variants", in the sense that the variants directly affect a trait (weakly, but directly), or "tag variants", which means that they are strongly correlated with other, unknown, variants that are causal, but that the tag variant itself does not have a direct effect on the phenotype.

PRSs can be calculated using either individual level data or summary statistic data. Strategies for PRS construction are expanding, but a well-accepted general approach to building an accurate PRS consists of deconvoluting the signal in all regions of association by investigating the combination of variants that best capture the underlying biological associations. This process assigns, for each association, probabilistic weights to each variant, thus describing which variant or variants are likely to be directly causal. This process is referred to as "fine-mapping", and several strategies have been previously proposed to achieve this task (see, for example, Benner et al, Bioinformatics 2016, 15; 32(10):1493-1501).

The number of associations will vary, with many genomic regions containing a single potential association while some genomic regions will contain multiple independent associations (up to 10 has been reported, though this is rare). A technical challenge in identifying the correct combination of variants responsible for all the associations in a region is that these variants can be correlated with each other. The larger the correlations are, the higher the number of samples will be required to break down these correlations.

Some tools to build PRSs are designed to take advantage of summary statistics data. One such approach refers to pruning and thresholding: the most associated variant is selected to contribute to a PRS and its highly correlated variants are removed. The most associated variant among the remaining variants is then picked, and the process is repeated until the significance of the remaining variants drops below a predefined threshold. A further approach, popularised by the LDpred software (https://github.com/bvilhjal/ldpred), iterates through multiple random selections of plausible variants genome-wide and, as variants are picked or removed, estimates the residual signal.

A strength of the summary statistics data based strategy is that the absence of limitation around sharing of individual level data means that much larger sample sizes can be made available to the scientific community. This is why much of the current PRS design is based on these large summary statistics datasets.

However, for all summary statistics data based methods, correlated variants are handled by referring to an external data source describing what the correlations between variants are expected to be. The pattern of correlations between genetic variants is referred to as linkage disequilibrium (LD). The correlations in these external data sources will not perfectly match the correlations that would be obtained from the individual level data used to generate the summary statistics data. This introduces additional uncertainty into the fine-mapping procedure due to the uncertainty about what the correct correlations should be. Therefore, summary statistics data based fine-mapping is fundamentally limited by the uncertainty about the underlying LD pattern.

Another limitation of relying on an external dataset to describe the pattern of LD is that different populations have distinct patterns of LD. Therefore, inferences made for one population are unlikely to be as precise for different populations. In other words, PRSs derived based on a reference LD dataset provide limited robustness to population variability.

It is an object of the invention to improve analysis of genetic data about an organism and/or allow more robust and/or accurate PRSs to be obtained for individuals.

While the pattern of LD varies between populations, a variant that impacts a trait or disease in one population will generally also impact that same trait/disease in a different population. Hence, using fine-mapping techniques to identify a causal variant or variants, or sets of variants that likely include or tag the causal variants or variants, will make the PRS more accurate, in particular by increasing its robustness to population variability.

However, not all variants can be fine-mapped, especially the large number of variants with small effects on the target phenotype. Therefore, alternative techniques that do not need to make precise statement about which variants are causal, but solely focus on the prediction problem, are also useful for PRS construction.

The accurate derivation of a PRS, which is potentially of high clinical utility in predicting disease, or predicting an individual's response to particular drugs or treatments, would therefore benefit from statistical techniques that leverage the benefit of fine-mapping, while also allowing the use of alternative machine learning technologies, when appropriate.

According to an aspect of the invention, there is provided a computer-implemented method of analysing genetic data about an organism to obtain information about the organism, the method comprising: receiving input data comprising strengths of association between one or more phenotypes including a target phenotype and a plurality of genetic variants in a region of interest of the genome of the organism; applying a fine-mapping algorithm to all or a subset of the input data to identify one or more independent phenotype-variant associations within the region of interest, comprising identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one; calculating, on the basis of the input data and the set of fine-mapped variants, a fine-mapping predictive model quantifying an effect on the target phenotype of the set of fine-mapped variants; subtracting from the input data, using the fine-mapping predictive model, the effect on the target phenotype of the set of fine-mapped variants to obtain residual association data; and applying a machine learning algorithm to the residual association data to identify further predictive correlations between the target phenotype and the plurality of genetic variants.

By using fine-mapping techniques to identify fine-mapped variants that are potentially causal for the target phenotype, and additionally analysing the residual signal (via the residual association data) that remains after the effect of the fine-mapped variants is accounted for, the method can take account of further weak correlations that may be present in the data. The inclusion of these additional correlations improves the predictive accuracy of the model.

In an embodiment the strengths of association comprise an estimated effect size of each of the plurality of genetic variants on the target phenotype, and a standard error of each of the estimated effect sizes. Estimated effect sizes and their errors are widely available as summary statistic data from a large number of studies, thereby allowing access to a large amount of data.

In an embodiment the step of receiving input data comprises: receiving individual level data comprising genotypes and corresponding phenotypes for each of a plurality of individuals; and determining using the individual level data an estimated effect size of each of the plurality of genetic variants on the target phenotype and a standard error of each of the estimated effect sizes. Individual level data may be used in some embodiments because it is not affected by underlying assumptions about correlations between variants within a region that may be present in summary statistic data, thereby reducing the chance of introducing unintentional bias or errors.

In an embodiment the identifying of the set of fine-mapped variants is performed using an iterative method, wherein each iteration comprises: identifying, on the basis of the input data, a fine-mapped variant within the region of the genome different from any previously identified fine-mapped variant; updating the input data to account for the effect on the target phenotype of the fine-mapped variants already identified, using a matrix of correlations between the genetic variants within the region of the genome; and determining whether to perform a further iteration on the basis of the updated input data. By using an iterative approach, multiple fine-mapped variants can be identified from residual signals not accounted for by a single fine-mapped variant, thereby maximising the use of the signals present in the summary data.

In an embodiment the identifying of the set of fine-mapped variants comprises using a plurality of instrument traits known to affect the target phenotype, the use of the instrument traits comprising: determining a set of fine-mapped variants for the instrument traits; and determining whether to include each of one or more of the fine-mapped variants for the instrument traits in the set of fine-mapped variants for the target phenotype on the basis of a relationship between the plurality of instrument traits and the target phenotype. The relationship between the plurality of instrument traits and the target phenotype may take account of potentially complex patterns of association between the instruments traits and the target phenotype. Alternatively or additionally, in other embodiments the identifying of the set of fine-mapped variants comprises identifying a set of fine-mapped variants for one or more directly causal instrument traits known to affect the target phenotype. In such cases it may not be necessary to take account of complex patterns of associations between multiple instrument traits and the target phenotype.

The use of instrument traits can improve the accuracy of determining fine-mapped variants for a phenotype where the genetic variants have only a small effect on the target phenotype, but a larger effect on the instrument trait.

In an embodiment, the calculating of the fine-mapping predictive model comprises: determining effect sizes on the one or more instrument traits of the set of fine-mapped variants for the one or more instrument traits, and determining an effect size for the target phenotype of each of the fine-mapped variants for the instrument traits included in the set of fine-mapped variants for the target phenotype on the basis of a predetermined relationship between effect sizes for the instrument traits and effect sizes for the target phenotype. Instrument traits can also be used to improve the estimation of effect sizes, where the effect of the genetic variant on the instrument trait is larger than on the target phenotype. This can be especially effective where the relationship between the instrument trait and the target phenotype is itself well-characterised.

In an embodiment, the effect on the target phenotype of the set of fine-mapped variants is inferred using a machine learning algorithm. In such an embodiment, the set of fine-mapped variants and their corresponding marginal effect sizes are input into the machine learning algorithm to generate effect sizes, such that the residual association data are the marginal effect sizes corresponding only to the set of fine-mapped variants. The set of fine-mapped variants may further comprise one or more variants known to have a high likelihood of being causal for the target phenotype.

This reduces the number of genetic variants that the machine learning algorithm is applied to by focussing it on the variants most likely to be causal. This reduces computational load and improves the efficiency of the method.

In an embodiment, the strengths of association comprise an estimated effect size of each of the plurality of genetic variants on the target phenotype, and a standard error of each of the estimated effect sizes; and the fine-mapping predictive model comprises a fine-mapped effect size on the target phenotype for each of the fine-mapped variants, the fine-mapped effect size being calculated from the estimated effect size of the fine-mapped variants taking account of the estimated probability of the fine-mapped variants being causal for the phenotype-variant association. Adjusting the effect sizes of the fine-mapped variants dependent on their probability of being causal ensures that the significance of a fine-mapped variant is not overestimated if it has a lower certainty of being causal.

In an embodiment the strengths of association comprise an estimated effect size of each of the plurality of genetic variants on the target phenotype, and a standard error of each of the estimated effect sizes; and the step of subtracting from the input data the effect on the target phenotype of the set of fine-mapped variants comprises obtaining a residual effect size for each of a plurality of the genetic variants in the input data, the residual association data comprising the residual effect sizes, wherein, after appropriate renormalisation of the effect sizes to ensure equal variance, the residual effect size $\hat{\beta}_i$ for genetic variant i is given by:

$$\hat{\beta}_i = \beta_i - \sum_{j=1}^{N} p_j r_{ij} \hat{\beta}_j$$

where $\beta_1$ is the estimated marginal effect size of genetic variant i, N is the number of fine-mapped variants, $p_i$ is the probability that variant j is causal, $\hat{\beta}_j$ is the fine-mapped effect size of the $j^{th}$ fine-mapped variant on the target phenotype, and $r_{ij}$ is a correlation between the $j^{th}$ fine-mapped variant and genetic variant i.

The above approach enables the residual effect of variants in the region of interest of the genome to be identified clearly for further analysis by the machine learning algorithm.

In an embodiment, the input data are derived from a plurality of different genetic studies, and the step of applying a machine learning algorithm to the residual association data comprises using a prior probability for each of the plurality of genetic variants of being causal for the target phenotype that is dependent on the consistency of the strength of association between each genetic variant and the target phenotype between the different genetic studies. Using a non-flat prior for the machine learning algorithm allows the method to improve its accuracy by accounting for further information about the certainty that particular data are reliable.

In an embodiment, the step of applying a machine learning algorithm to the residual association data comprises using a prior probability for each of the plurality of genetic variants of being causal for the target phenotype that is dependent on genomic annotations of the plurality of genetic variants in the region of interest. Including genomic annotations provides further data about the likelihood of particular variants being causal for the target phenotype, thereby improving the determination of effect sizes.

In an embodiment, the method further comprises a step of calculating a polygenic risk score for an individual for the target phenotype using the fine-mapping predictive model and the further predictive correlations identified by the machine learning algorithm.

Accounting for the further correlations identified by the machine learning algorithm improves the accuracy of the PRS by allowing the method to take account of residual signals that are not explained by the set of fine-mapped variants.

In an embodiment, the input data are derived from a plurality of different populations of the organism, and either or both of the following is satisfied: the calculating of the fine-mapping predictive model is performed separately for portions of the input data corresponding to different populations to obtain multiple respective population-matched fine-mapping predictive models; and the applying of the machine learning algorithm to the residual association data is performed separately for portions of the input data corresponding to different populations to obtain multiple respective sets of population-matched further predictive correlations.

Providing fine-mapping predictive models and sets of further residual predictive correlations that are matched to particular populations allows the method to account for possible variations in linkage disequilibrium (correlations between variants) within the region of interest of the genome.

In an embodiment, the method further comprises receiving input data from an individual having genes from a mixture of the different populations; and calculating a polygenic risk score for the individual by performing either or both of: matching each of multiple population-matched fine-mapping predictive models to a corresponding portion of the input data that matches the population of the population-matched fine-mapping predictive model and applying each matched fine-mapping predictive model to the corresponding portion of the input data; and matching each of multiple sets of population-matched further predictive correlations to a corresponding portion of the input data that matches the population of the set of population-matched further predictive correlations and applying each matched set of further predictive correlations to the corresponding portion of the input data.

Calculating the polygenic risk score for an individual using multiple fine-mapping predictive models and/or sets of further residual predictive correlations that are matched to different multiple respective portions of the input data from the individual allows the method to provide more accurately predictive risk scores that take account of the systematic differences in correlations between variants associated with different populations.

In an embodiment, the method further comprises receiving input data from an individual having genes predominantly from one of the different populations; and calculating a polygenic risk score for the individual by performing either or both of: applying a population-matched fine-mapping predictive model to all of the input data from the individual, the population-matched fine-mapping predictive model being matched to the population of the individual; and applying a set of population-matched further predictive correlations to all of the input data from the individual, the set of population-matched further predictive correlations being matched to the population of the individual.

Calculating the polygenic risk score using fine-mapping predictive models and sets of further residual predictive correlations that are matched to the population of the individual allows the method to provide more accurately predictive risk scores that take account of systematic differences in correlations between variants associated with different populations.

In an embodiment, the identifying of the one or more fine-mapped variants by the fine-mapping algorithm takes account of associations between the plurality of genetic variants and phenotypes other than the target phenotype.

Using information about correlations with other phenotypes maximises the amount of the available information that can be used to identify the fine-mapped variants and their effect sizes. This further improves the accuracy of the results of the method.

According to an alternative aspect, there is provided an apparatus for analysing genetic data about an organism to obtain information about the organism, the apparatus comprising: a receiving unit configured to receive input data comprising strengths of association between one or more phenotypes including a target phenotype and a plurality of genetic variants in a region of interest of the genome of the organism; and a data processing unit configured to: apply a fine-mapping algorithm to all or a subset of the input data to identify one or more independent phenotype-variant associations within the region of interest, by identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one; calculate, on the basis of the input data and the set of fine-mapped variants, a fine-mapping predictive model quantifying an effect on the target phenotype of the set of fine-mapped variants; subtract, using the fine-mapping predictive model, the effect on the target phenotype of the set of fine-mapped variants from the input data to obtain residual association data; and apply a machine learning algorithm to the residual association data to identify further predictive correlations between the target phenotype and the plurality of genetic variants.

Embodiments of the invention will be further described by way of example only with reference to the accompanying drawings, in which.

Figure 4:
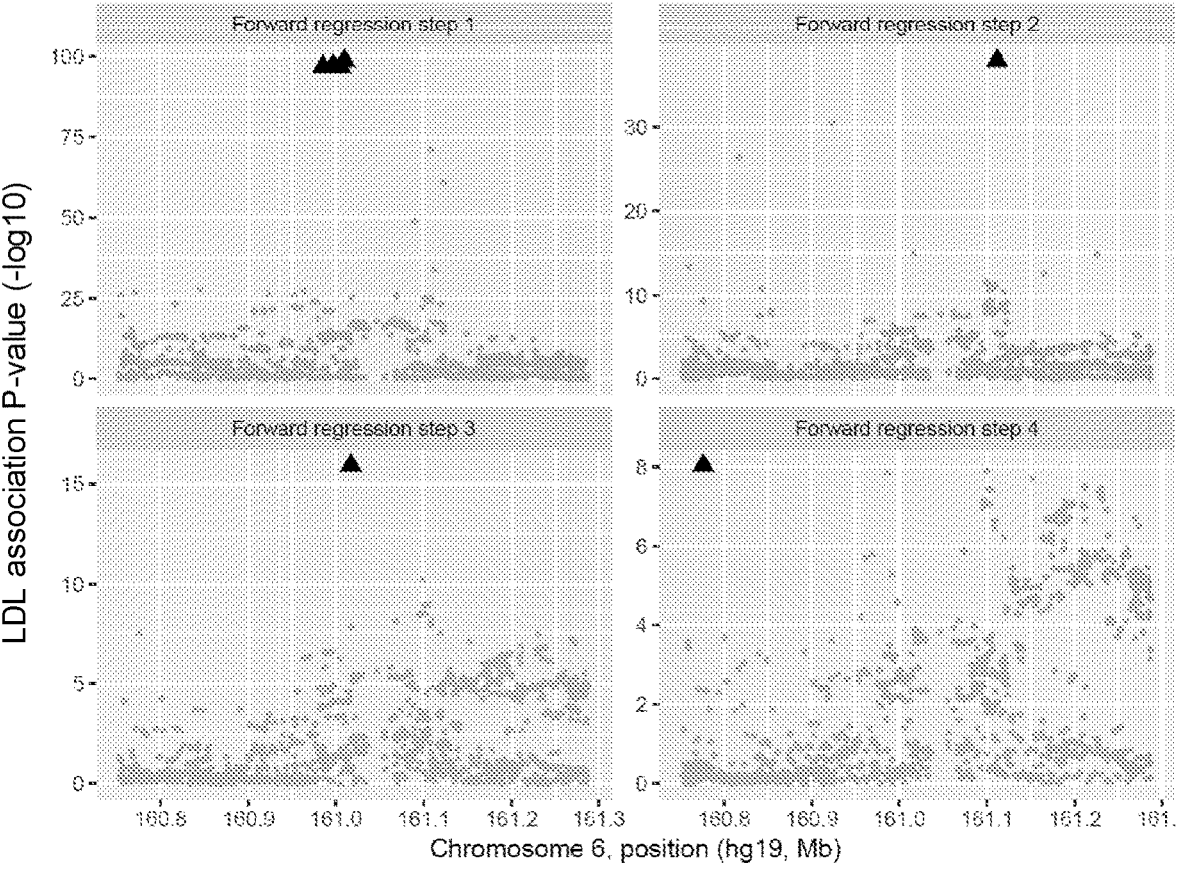
FIG. 4 shows four graphs representing steps in a stepwise forward regression analysis for identifying four respective independent association signals for identifying fine-mapped variants associated with LDL in the LPA region of chromosome 6.
Figure 5:
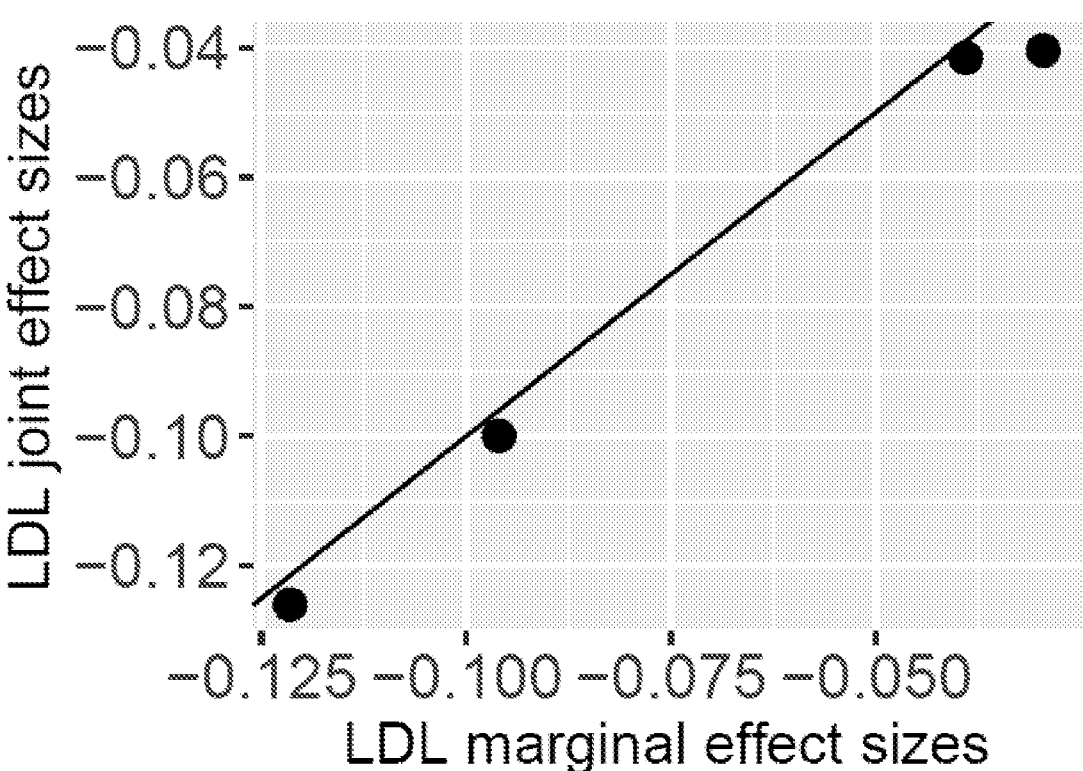
FIG. 5 is a graph depicting joint versus marginal LDL effect size estimation for the four association signals identified in FIG. 4.
Figure 6:
Figure 7:
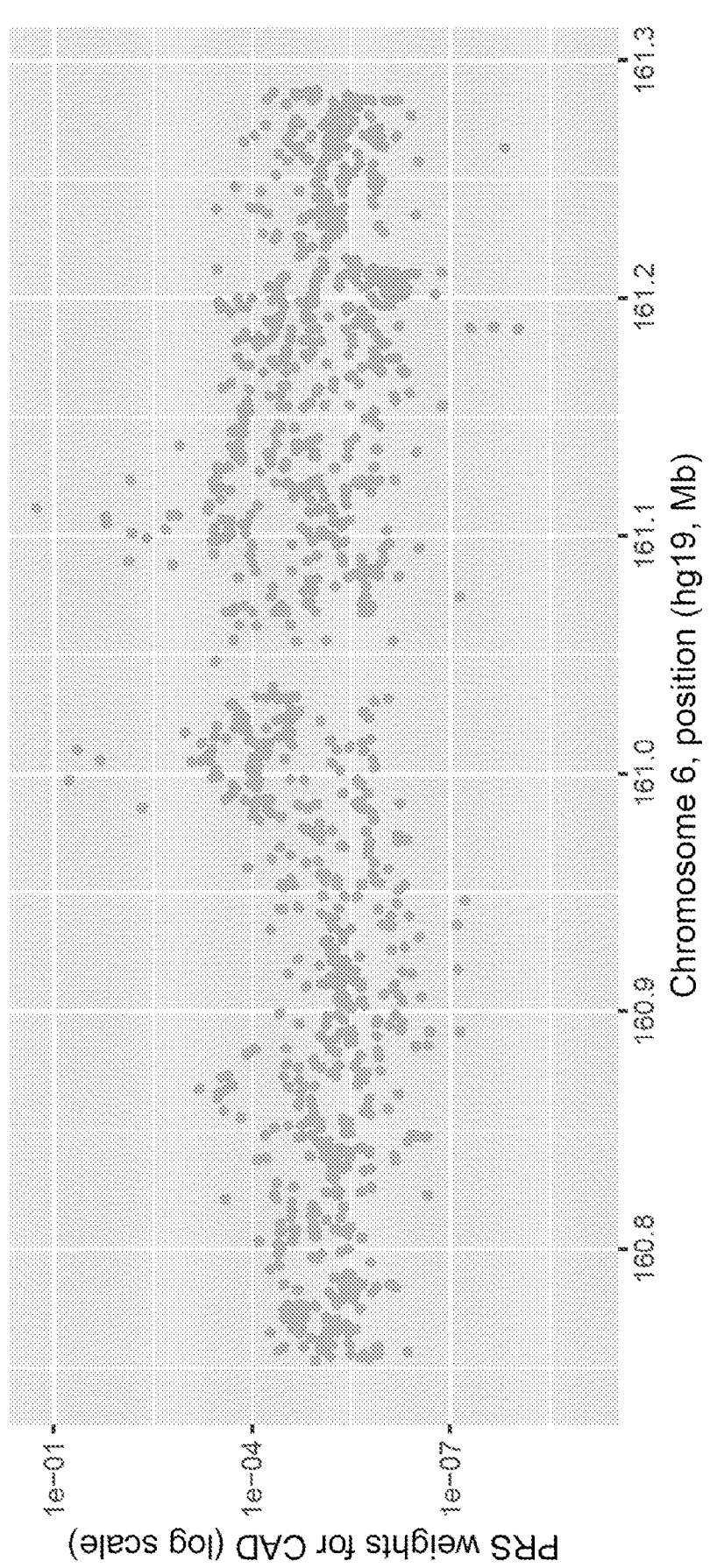

FIG. 6 is a graph depicting CAD PRS weights for the LPA region of chromosome 6 obtained by applying the LDpred machine learning algorithm to residual association data obtained using the analysis of FIGS. 4 and 5; and FIG. 7 is a graph depicting CAD PRS weights for the LPA region of chromosome 6 obtained by applying the LDpred machine learning algorithm directly to CAD variant data without any preceding fine-mapping step.

Figure 1:
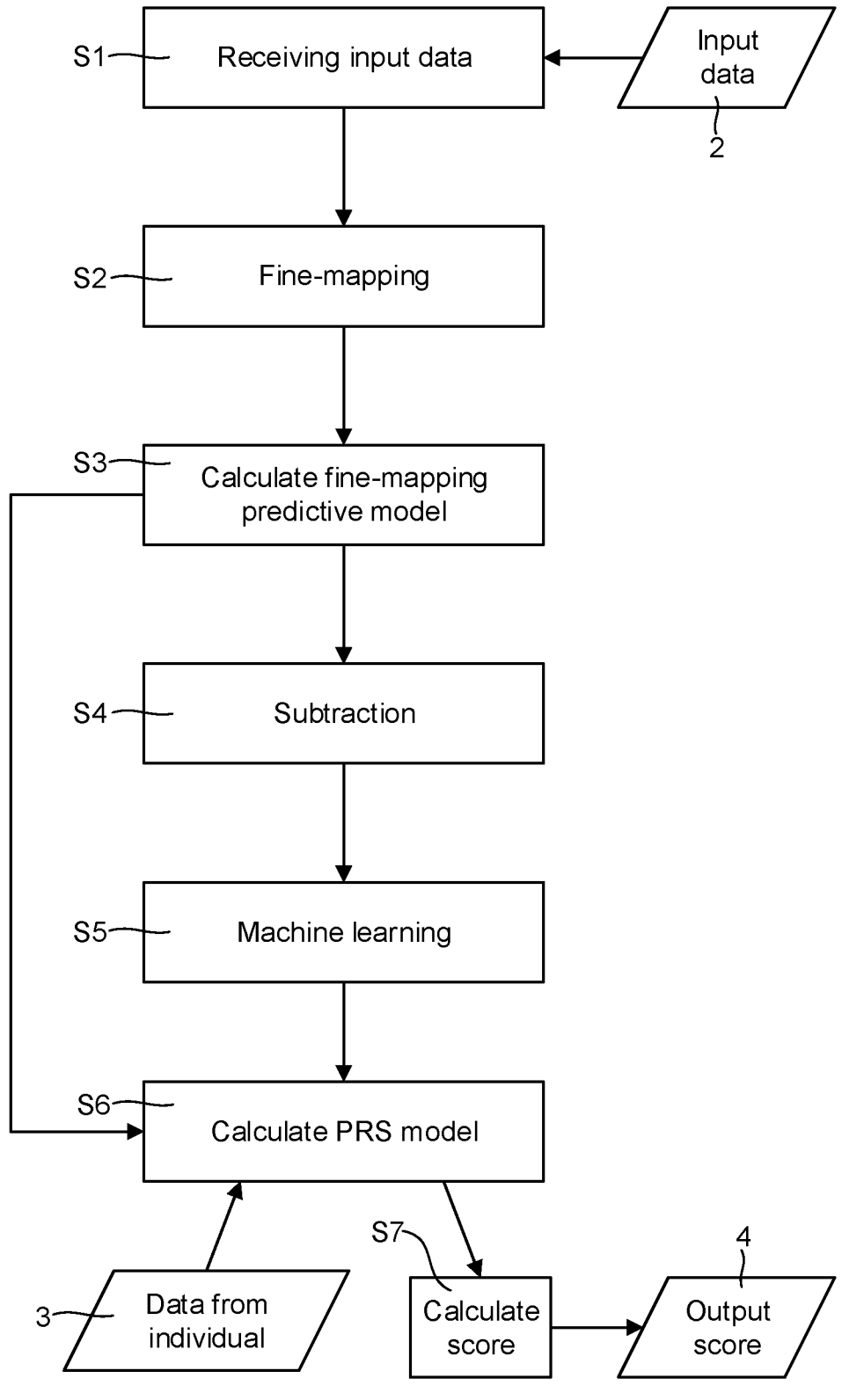
FIG. 1 is a flow chart depicting a method of analysing genetic data to obtain information about an organism.
Figure 2:
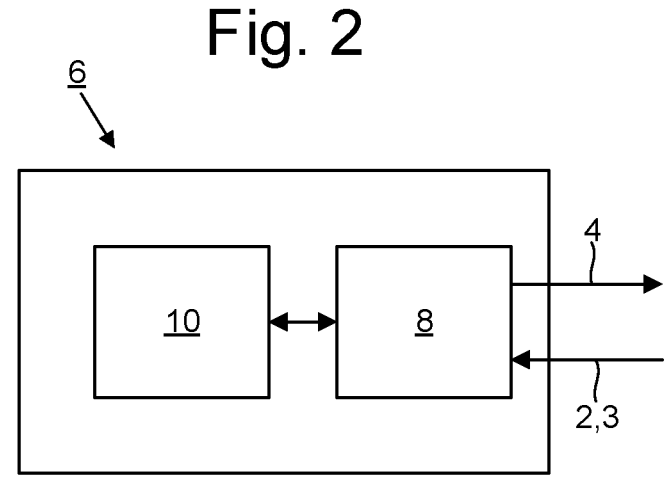
FIG. 2 depicts an apparatus for analysing genetic data to obtain information about an organism.

Embodiments of the disclosure relate to computer-implemented methods of analysing genetic data about an organism to obtain information about the organism. FIG. 1 depicts a framework for these methods. FIG. 2 depicts an apparatus 6 for performing the methods.

In step S1, input data 2 is received (e.g. by a receiving unit 8 of the apparatus 6). The receiving unit 8 may comprise a data communication interface. The data communication interface allows the input data 2 to be provided to a data processing unit 10 of the apparatus 6. The data processing unit 10 may comprise any suitable combination of computer hardware, firmware and/or software configured to perform the data processing functions described below. A computer program, optionally provided on a computer-readable medium, may be provided comprising instructions for performing any of the methods described below. The apparatus 6 is depicted as a standalone unit (e.g. a single PC or workstation) but this is not essential. In other embodiments the apparatus 6 comprises a distributed computing system comprising multiple computers connected by a network.

In some embodiments, the input data 2 comprises strengths of association between one or more phenotypes including a target phenotype and a plurality of genetic variants in a region of interest of the genome of the organism. In some embodiments, the input data 2 comprises either or both of GWAS summary statistics and individual level data. As will be described in further detail below, the method may use the input data 2 to (i) identify variants with high confidence of having a direct causal effect on a target phenotype (referred to as fine-mapped variants); and (ii) obtain residual association data (which may be referred to as a residual signal and/or be derived from a residual signal) after conditioning on the high confidence variants and/or predict trait risk (e.g. in the form of a PRS) for individuals. The method is particularly advantageous when used in embodiments where the organism is a human.

The target phenotype may be any phenotype of interest that has been the subject of a GWAS or for which associated individual level genetic data are available. Examples of such phenotypes are many, and include: a level of expression, and regulation of expression, of a gene (and related nucleotide sequences); epigenetic characteristics (for example, nucleotide modification, chromosomal conformation); a level of abundance of a protein or peptide; the function and/or molecular structure of a protein or peptide; a quantity of a molecule in the organism (for example a drug, a hormone, a DNA molecule, or an RNA molecule, a metabolite, a vitamin); characteristics of biochemical and metabolic processes (for example basal metabolic rate, prothrombin time, activated partial thromboplastin time); cellular morphology and function (for example, red blood cell mean corpuscular volume, absolute neutrophil count); tissue morphology and function (for example, bone mineral density, hair colour); organ and organ system morphology and function (for example, left ventricular ejection fraction, forced vital capacity); any response to an external stimulus or stimuli (for example light, sound, touch or any other sensory input); any response to exposure to a substance or pathogen (for example dietary input, drugs, gases, viruses, bacteria); behavioural and lifestyle characteristics (for example, smoking, alcohol consumption, occupation); reproductive and life course characteristics and function (for example age at menarche, placental weight, number of years in education); the onset, trajectory, and prognosis of a disease or condition (for example diabetes, cardiovascular disease, obesity); a measurable anatomical characteristic (for example, body-mass index, lean muscle mass, body fat percentage); a measurable physiological or functional characteristic (for example, heart rate, blood pressure, intelligence); and measurable psychological or cognitive characteristics (for example, metrics of fluid intelligence, psychotic symptoms). Any of these measurements might be absolute or relative. Phenotypes are also often referred to as traits.

In step S2, a fine-mapping algorithm is applied to all or a subset of the input data 2. In an embodiment, the fine-mapping step identifies variants with high confidence of being causal, thereby obtaining a set of fine-mapped variants. Further details about step S2 are given later.

In step S3, a fine-mapping predictive model is calculated based on the input data 2 and the fine-mapped variants. The fine-mapping predictive model quantifies effect sizes of the fine-mapped variants on the target phenotype. Effect size refers to how much a given variant impacts disease risk (or more generally the "risk" of having or developing any given phenotype). For example, an effect size of 1.2 means a 20% increase in risk per risk allele (which can be encoded as 0, 1 or 2 for each individual) for that given variant. The quantification of the effect sizes thus allows the fine-mapping predictive model to make predictions about an individual based on genetic data from the individual. Further details about S3 are given later.

In step S4, the fine-mapping predictive model is used to subtract from the input data 2 the effect on the target phenotype of the set of fine-mapped variants to obtain residual association data. Further details about step S4 are given later.

In step S5, a machine learning algorithm is applied to the residual association data to identify further predictive correlations between the target phenotype and the plurality of genetic variations of the input data 2. In the specific example below a machine learning algorithm called LDpred is used. LDpred is well known in the art of fine-mapping and PRS generation. Software for implementation is available at https://github.com/bvilhjal/ldpred. The further predictive correlations may quantify effect sizes associated with variants other than the fine-mapped variants (after the effect of the fine-mapped variants has been taken account of), thereby allowing predictions about an individual to be refined relative to if only the fine-mapping predictive model was applied to genetic data from the individual.

In step S6, a PRS model is evaluated. The PRS model may be derived partly from the fine-mapping predictive model from step S3 and partly from the further predictive correlations from the machine learning performed in step S5. As will be described below, the combination of the fine-mapping predictive model and the further predictive correlations from the machine learning may define a recipe for calculating a PRS that takes the form of a weighted sum over variants, where the weights for fine-mapped variants are provided by the fine-mapping predictive model and the weights for other variants are provided by the further predictive correlations from the machine learning. This is possible where the trained machine learning algorithm can be interpreted in terms of such a weighted sum over variants. In other embodiments, the trained machine learning algorithm may be more complex and therefore be represented in a different way as part of the PRS model.

The PRS model calculated in step S6 may be used to calculate a PRS score based on genetic data from an individual. The PRS model may be output as data representing the PRS model (e.g. via the data communication interface of the apparatus 6 of FIG. 2). The steps leading up to and including the step S6 (including training of the machine learning algorithm) may thus be performed on one apparatus 6 and the subsequent steps involving use of the PRS model (e.g. for calculating PRS scores for individuals) may be performed on other apparatus (not shown) comprising any suitable combination of computer hardware, firmware and/or software capable of performing the necessary data processing tasks. Alternatively, the calculation of the PRS score may be performed on the same apparatus 6 that calculated the PRS model.

In step S7, the PRS model calculated in step S6 is used to calculate a PRS score for an individual. The PRS score may be output as data 4 representing the PRS score.

The calculated PRS model constitutes information about an organism at a general level (e.g. about humans generally) in the sense that it enables a PRS score to be calculated from genetic information obtained from any individual. The PRS score constitutes information about a specific individual organism (e.g. a single human subject).

Example Application Scenario

FIGS. 3-7 depict use of the method of FIG. 1 in an example scenario and will be referred to in the more detailed discussion of the method steps given below.

Figure 3:
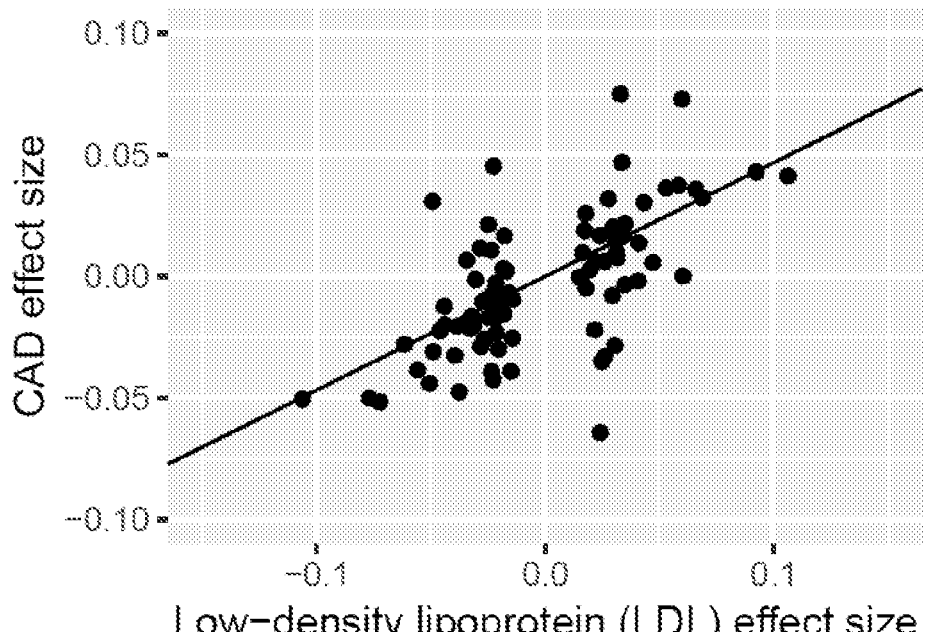
FIG. 3 is a graph showing an effect size comparison between coronary artery disease (CAD) and low-density lipoprotein (LDL)

FIG. 3 illustrates how effect sizes for LDL are correlated with effect sizes for CAD at 95 distinct loci associated with LDL. This correlation is observed in part because LDL is understood to have an almost direct causal impact on CAD. We therefore refer to LDL as an appropriate instrument for CAD, which implies that information about LDL can be used to improve the accuracy of a PRS for CAD.

FIG. 4 illustrates the outcome of fine-mapping of LDL using the method of FIG. 1 in the LPA region of chromosome 6 using an established methodology (stepwise forward regression). Each regression step identifies an additional independent phenotype-variant association, with four independent phenotype-variant associations being identified in total. In each plot the black triangles represent the newly identified fine-mapped variant or credible set (CS) of fine-mapped variants. At each step, genetic variants with low fine-mapping probability (<1%) are in grey. The first LDL association signal has four fine-mapped variants with posterior probability greater than 1%, whereas the remaining three LDL association signals identify a single fine-mapped variant with fine-mapping probability >1%.

FIG. 5 shows that for the LDL instrument trait of this example, four jointly estimated effect sizes estimated from the four independent phenotype-variant associations shown in FIG. 4 differ slightly from four marginally estimated effect sizes.

FIGS. 6 and 7 depict derived PRS weights for CAD for the same LPA region in chromosome 6. In FIG. 6, the fine-mapped CAD variants were extrapolated from the LDL fine-mapping and effect sizes (FIGS. 4 and 5) and subtracted from the CAD data prior to an LDpred analysis to capture a residual signal (representing further predictive correlations). FIG. 6 therefore combines PRS weights derived from LDL fine-mapping (black) with PRS weights derived from the LDpred residual signal (grey). This contrasts with FIG. 7, for which the standard LDpred analytical strategy based on CAD alone was applied without the initial fine-mapping step. One of the consequences of the limited accuracy of the process without the initial LDL fine-mapping is that the fourth signal is not detected in FIG. 7. This is because the CAD data alone are not sufficient to characterise this association.

Further example implementation details for steps S2-S7 of FIG. 1 are given below, with references being made where appropriate to the above example application scenario for illustrative purposes.

Step S2: Fine-Mapping

As mentioned above, in step S2 the method applies a fine-mapping algorithm to all or a subset of the input data 2 to identify one or more independent phenotype-variant associations within the region of interest. The identifying of one or more independent phenotype-variant associations within the region of interest may comprise identifying high-confidence fine-mapped variants, which are variants having a high confidence of either being a causal variant, or a tag variant of a causal variant, for the phenotype of interest. For each association a set of one or more fine-mapped variants is identified from the plurality of genetic variants, FIG. 4 illustrates application of a fine-mapping algorithm in the context of the example application scenario discussed above. The fine-mapping algorithm in this case identifies four independent phenotype-variant associations for LDL within a region on chromosome 6 (one for each of the four plots shown).

Fine-mapping algorithms are typically designed to capture the underlying causal biology for the target phenotype by locating the causal variant or variants, or alternatively a credible set or sets of variants that include or closely tag the causal variant or variants. Fine-mapping algorithms contrast with alternative purely predictive approaches, typically based on machine learning techniques such as LASSO, random forests or neural networks, that capture predictive signals without providing a discrete summary of the data that maps to the underlying biology.

The phenotype-variant associations are independent in the sense that even though there may exist some degree of correlation between two identified variants the association of a second fine-mapped variant with a phenotype is not solely due to its correlation with the first fine-mapped variant that is associated with the phenotype. In other words, the second fine-mapped variant is associated with the phenotype even after taking into account or conditioning on the first fine-mapped variant that is associated with the phenotype. In comparison, multiple variants within a CS are not independent of one another because if we chose one of the variants within the CS and conditioned on this variant the association at all other variants within the CS would disappear i.e. the multiple associations only exist due to high correlation between the variants.

Each independent phenotype-variant association may be linked to either a single fine-mapped variant, or a credible set (CS) of (multiple) fine-mapped variants. For each association a set of one or more fine-mapped variants is thus identified from the plurality of genetic variants. A CS of fine-mapped variants is a set of two or more fine-mapped variants which are considered to have a high likelihood of being causal for the target phenotype. The method determines for each fine-mapped variant an estimated probability of being causal for the phenotype-variant association, the sum of the probabilities for the fine-mapped variants within the set adding to one. Where only one fine-mapped variant is identified, the estimated probability will simply be one for that fine-mapped variant. In FIG. 4, forward regression steps 2-4 display examples of identifying a single fine-mapped variant whilst forward regression step 1 identifies a CS of fine-mapped variants.

In some embodiments, the identifying of the one or more fine-mapped variants by the fine-mapping algorithm takes account of associations between the plurality of genetic variants and phenotypes other than the target phenotype. The input data 2 for such embodiments would thus comprise strengths of association between plural phenotypes and the plurality of genetic variants in the region of interest of the genome of the organism. Using associations with plural phenotypes facilitates leveraging of data from a large number of studies, which may encompass a wide range of different phenotypes and make use of the fact that many traits can share the same causal variant.

In an embodiment, the input data 2 comprises data describing the association between individual variants and the target phenotype in the form of a marginal variant effect size and standard error. In such an embodiment, the strengths of association may comprise an estimated effect size of each of the plurality of genetic variants on the target phenotype, and a standard error of each of the estimated effect sizes. The estimated effect sizes are marginal variant effect sizes. The marginal variant effect size refers to the impact of the variant when considered in isolation, i.e. ignoring the impact of nearby correlated variants. For example, a tag variant can have a strong marginal effect size but its "true" effect size is zero. Input data of this format is commonly referred to as summary statistics data.

In an embodiment, the application of the fine-mapping algorithm to all or a subset of the input data 2 to identify one or more independent phenotype-variant associations within the region of interest comprises the following. By using a probabilistic model (e.g. a Bayesian statistical model) within a given DNA region (i.e. region of the genome of the organism), studies (each containing data about the strength of association between a target phenotype and one or more genetic variants) are assigned to clusters, with each cluster assumed to have a similar pattern of causal variation. A Markov chain Monte Carlo algorithm or similar is then used to explore the space of possible cluster assignments. Once a set number of iterations that assigns studies to clusters has been performed, the set of characteristics of the cluster may be used to identify a single variant or a CS of genetic variants (i.e. a set of one or more fine-mapped variants) that are likely to be causal for the phenotypes assigned to the corresponding cluster. Using this method based on a large number of phenotypes increases the power and the accuracy with which variants that impact phenotypes are identified.

Further details of a method of this type can be found in PCT application number PCT/GB2019/050525.

In some cases, the method identifies at most a single fine-mapped variant or a single CS of fine-mapped variants for a given DNA region. However, there may exist more than one independent fine-mapped variant (or correspondingly more than one CS) that are likely to be causal within a region. Identification of these additional independent fine-mapped variants will provide additional predictors of the disease or trait of interest, and therefore improve the ability to predict an individual's risk of developing a disease or trait.

Alternative Implementation of Step S2 when Only Summary Statistic Data is Available It is possible to identify additional independent fine-mapped variants when only summary statistics data are available. In an embodiment, this is achieved by considering the correlation between genetic variants within a region of the genome, usually summarised by the "LD matrix", the matrix of correlations $r_{ij}$ of genotypes $g_i$ and $g_j$ at locations i, j, often obtained from subpopulations of a reference panel such as the 1000 Genomes consortium, or the Haplotype Reference Consortium. Methodologies such as FINEMAP (Benner et al, Bioinformatics 2016, 15; 32(10):1493-501) can be suitably adapted to this setting where we consider large numbers of studies and phenotypes.

Another such embodiment would identify additional causal variants (referred to herein as fine-mapped variants) by updating the summary statistics data to account for the effect of fine-mapped variants already identified within a DNA region, and then assessing the residual evidence for an additional fine-mapped variant. In this case, identifying the set of fine-mapped variants is performed using an iterative method. Each iteration comprises identifying, on the basis of the input data, a fine-mapped variant within the region of the genome different from any previously identified fine-mapped variant, updating the input data to account for the effect on the target phenotype of the fine-mapped variants already identified, using a matrix of correlations between the genetic variants within the region of the genome, and determining whether to perform a further iteration on the basis of the updated input data (e.g. stopped when it is determined that the updated input data no longer contain any information of interest, such as when a predetermined significance threshold is no longer exceeded and/or P-values are all relatively flat).

The approach can be applied iteratively to explore the space of fine-mapped variants within a DNA region by proposing the addition or removal of at most one fine-mapped variant (https://projecteuclid.org/euclid.aoas/1507168840). Therefore, in some embodiments, the step of identifying a fine-mapped variant different from any previously identified fine-mapped variant comprises removing a previously identified fine-mapped variant from the set of fine-mapped variants. Further details of these methods can be found in PCT application number PCT/GB2019/050525.

Alternative Implementation of Step S2 Using Individual Level Data

An alternative fine-mapping strategy is to perform fine-mapping with individual level data. In such an embodiment, the step of receiving input data comprises receiving individual level data comprising genotypes and corresponding phenotypes for each of a plurality of individuals, and determining using the individual level data an estimated effect size of each of the plurality of genetic variants on the target phenotype and a standard error of each of the estimated effect sizes. This could be achieved using stepwise regression methodology to explore the space of fine-mapped variants using forward selection, backward elimination or a combination of the two.

Alternatively, the individual level data could be used in combination with the summary statistics data, leveraging the information obtained from a summary statistics based fine-mapping method such as that described in PCT application number PCT/GB2019/050525. One way that this could be achieved is to use the single fine-mapped variant/CS obtained from a method such as that described in PCT application number PCT/GB2019/050525, and condition on these in subsequent stepwise regression steps (as before a combination of forward selection and backward elimination can be used).

Alternatively, residual summary statistics data derived from individual level data, conditioned on already identified fine-mapped variants can be obtained. In this way, the effect of variants already identified as high confidence fine-mapped variants is removed, making it possible to use residual correlations to identify further fine-mapped variants.

This is conducted in a similar way to the conditioning performed on summary statistics data when individual level data is not available, with a major advantage that LD information is not required. These derived residual summary statistics data can be used as input for a method such as that described in PCT application number PCT/GB2019/050525. This procedure can be iteratively repeated. This methodology can be based using only summary statistics data derived from individual level data or in combination with residual summary statistics data derived using LD panels from studies where individual level data does not exist.

Alternative Implementation of Step S2 Using One or Multiple Instrument Traits

An alternative implementation of step S2 takes advantage of instrument studies, so that identifying the set of fine-mapped variants comprises using one or more instrument traits known to affect the target phenotype. We define a trait as an instrument for a target phenotype when the trait is strongly correlated to the trait of interest. A special case is an instrument that is directly causal/modifying for the target phenotype. For example, LDL can be considered as an instrument trait for coronary artery disease, and coronary artery disease is an instrument trait for overall survival. An instrument study provides information on the strength of association between an instrument trait and the plurality of genetic variants which are being considered with respect to the target phenotype.

In many cases, the effect of a variant on the target phenotype will be too small to identify a credible set (CS) for the target phenotype. However, the effect may be sufficient for fine-mapping to be achievable using an appropriately powered instrument study. In other words, because the effect of the variant on the instrument trait is larger than the effect of the variant on the target phenotype, it is easier to accurately determine whether the variant is causal for the instrument trait. In that context, the fine-mapping and causal signal identification will be solely based on the instrument study, hence providing information about the target phenotype that would otherwise not be characterised.

Based on the above insight, in an embodiment the identifying of the set of fine-mapped variants comprises identifying a set of fine-mapped variants for one or more directly causal instrument traits known to affect the target phenotype. This is a relatively simple way of using instrument traits to supplement the fine-mapping of step S2, but requires that known directly causal instrument traits are available. In other embodiments, the identifying of the set of fine-mapped variants comprises using a plurality of instrument traits known to affect the target phenotype. The method then comprises determining a set of fine-mapped variants for the instrument traits and determining whether to include each of one or more of the fine-mapped variants for the instrument traits in the set of fine-mapped variants for the target phenotype on the basis of a relationship between the instrument traits and the target phenotype. In this case, the relationship between the plurality of instrument traits and the target phenotype may take account of potentially complex patterns of association between the instrument traits and the target phenotype, allowing use to be made of instrument traits that are not necessarily directly causal instrument traits.

FIGS. 3-5 provide an example in which fine-mapping is performed for LDL, which is an instrument trait for CAD, and the fine-mapped variants identified for LDL (FIG. 4) are used in subsequent steps where CAD is used as the phenotype of interest (FIG. 6).

Step S3: Calculating Fine-Mapping Predictive Model (e.g. to Estimate Effect Sizes for Fine-Mapped Variants)

As mentioned above, in step S3 the method calculates, on the basis of the input data 2 and the set of fine-mapped variants (identified in step S2), a fine-mapping predictive model. The fine-mapping predictive model quantifies an effect on the target phenotype of the set of fine-mapped variants. The effect on the target phenotype may be quantified using fine-mapped effect sizes for the target phenotype, in which case the fine-mapping predictive model consists of or comprises a fine-mapped effect size on the target phenotype for each of the fine-mapped variants that accounts for correlations between variants.

In embodiments where the strengths of association comprise summary statistics data (e.g. an estimated effect size of each of the plurality of genetic variants on the target phenotype, and a standard error of each of the estimated effect sizes), the fine-mapped effect sizes can be directly obtained from the marginal summary statistics data from a single GWAS for the target trait (i.e. target phenotype). When a single fine-mapped variant is identified within a region, the effect size reported in the GWAS summary statistics data may be used. When a CS of variants is identified, the GWAS summary statistics data may be weighted according to the probability (relative the rest of the variants in the CS) that the variant is causal. In some embodiments, each fine-mapped effect size may therefore be calculated from an estimated effect size (e.g. derived from the input data 2) of the fine-mapped variant taking account of the estimated probability of the fine-mapped variant being causal for the phenotype-variant association (e.g. derived from the input data 2, for example as a weighting as described above). For example, the fine-mapped effect size may be derived based on multiplying the estimated effect size by the probability of the fine-mapped variant being causal.

Alternative Implementation of Step S3 in the Presence of Correlated Associations When multiple credible sets, capturing several independent biological associations, are identified in the same DNA region, a correction is desirably applied to the effect sizes to control for the correlations between the associations. The corrected effect sizes are commonly referred to as joint effect sizes. This is illustrated in our fine-mapping example of the LPA region of chromosome 6 described above with reference to FIG. 4. FIG. 5 shows that for our LDL instrument trait, the four jointly estimated effect sizes differ slightly from the four marginally estimated effect sizes. If the associations were tightly correlated, the differences could be substantial.

When multiple fine-mapped variants are associated with a trait independently of one another, there might still be some correlation between them. The marginal effect sizes of these independent fine-mapped variants need to be adjusted to account for the correlation between the variants. So in other words the joint effect sizes are the effect sizes of multiple variants for one trait taking into account the correlation between the variants e.g. the four fine-mapped variants in the LDL example taking into account that there is some correlation between those four variants.

This correction for joint effect size estimation can be applied using summary statistics data (as described in Yang et al, Nature Genetics 2012, 44(4): 369-75) provided that the pattern of variant correlations (or LD) in the DNA region, which is population specific, is well characterised. Alternatively, this correction can be applied using individual level data, whereby all selected fine-mapped variants identified within a DNA region are jointly fitted using a regression model. This correction is necessary if several distinct associations are linked to credible sets of variants that are correlated.

Alternative Implementation of Step S3 Using One or Multiple Instrument Traits

An alternative methodology for effect size estimation leverages instrument studies. In an embodiment of this type, the identifying of the set of fine-mapped variants in step S2 comprises determining a set of fine-mapped variants for one or more instrument traits known to affect the target phenotype. The calculating of the fine-mapping predictive model then comprises determining effect sizes on the one or more instrument traits of the set of fine-mapped variants for the one or more instrument traits, and determining an effect size for the target phenotype of each of the fine-mapped variants for the instrument traits included in the set of fine-mapped variants for the target phenotype on the basis of a predetermined relationship between effect sizes for the instrument traits and effect sizes for the target phenotype. Because the impact of a genetic variant on the instrument trait is higher than on the target phenotype, it is easier to estimate the effect size of that variant on the instrument trait than on the target phenotype.

Thus, if external or genome-wide data allow the accurate characterisation of the relationship between instrument trait and target phenotype effect sizes, it is possible to leverage the better estimated effect size for the instrument trait in order to more accurately estimate the effect size for the target phenotype. One way to characterise the relationship between the instrument trait and the target phenotype effect sizes is to perform linear regression on the effect sizes for variants that are defined to be fine-mapped for both the instrument trait and target phenotype.

FIG. 3 shows an example in which the relationship between the effect sizes for LDL and CAD is inferred using a large set of LDL associated variants. LDL acts as an instrument trait for CAD in this example.

Alternative Implementation of Step S3 Using all Studies/Phenotypes as Potential Instrument Traits An alternative to step S3 is to take the independent fine-mapped variants (or CS) identified for all studies used to train the probabilistic model described above (and as detailed in PCT application number PCT/GB2019/050525). This results in a set of variants that are likely to be causal for at least one disease/trait.

The machine learning algorithm of step S5 can then be applied to this set of variants (typically the number of variants in this set is much smaller than the number used for step S5). Thereby, the effect on the target phenotype of the set of fine-mapped variants is inferred using a machine learning algorithm, which is preferably the same algorithm as used in step S5. The input of this embodiment of step S3 are the marginal effect sizes for each of the fine-mapped variants i.e. no signal subtraction has been applied at this stage. The output of this embodiment of step S3 is identical to that of step S5, namely a set of weights based on the residual effect sizes accounting for the uncertainty of the effect size estimate and the probability that the variant is causal for the focal phenotype. These weights computed for the subset of fine-mapped variants are then subtracted from the effect sizes for the plurality of genetic variants, thereby generating residual association data comparable to other embodiments of step S4.

In some embodiments, the set of fine-mapped variants can be combined with a set of variants reported in literature with high likelihood of being causal for diseases/traits. Thereby, the set of fine-mapped variants further comprises one or more variants known to have a high likelihood of being causal for the target phenotype.

Alternative Implementation of Step S3 Using Cross Population Data

An assumption can be made about the consistency of effect sizes across populations. At one extreme, we can assume that the effect sizes are constant across populations. At another extreme, if sufficient data are available, only population-specific datasets can be used to estimate effect sizes, using any of the aforementioned methods in the matching population.

An intermediate process is a hierarchical model that borrows information about effect sizes across populations, while allowing for some variability in inferred effect sizes if the data support this.

Steps S4 and S5: Subtraction and Machine Learning

In steps S4 and S5, the method comprises subtracting from the input data 2, using the fine-mapping predictive model, the effect on the target phenotype of the set of fine-mapped variants to obtain residual association data, and applying a machine learning algorithm to the residual association data to identify further predictive correlations between the target phenotype and the plurality of genetic variants.

In an embodiment, the machine learning algorithm comprises the model proposed by LDpred and only requires summary statistics data to identify the residual signal.

In that exemplary context we define three types of effect sizes for each variant:

$\beta_i$ refers to the marginal effect of variant i, which is the estimated effect size from summary statistic data when summary statistic data is used;

$p_j$ refers to the probability that the fine-mapped variant j is causal (the sum of the probabilities within a credible set adds up to 1).

$\tilde{\beta}_j$ refers to the inferred causal effect of fine-mapped variant j based on the fine-mapping step, hence corresponds to the estimated fine-mapped effect size of the $j^{th}$ fine-mapped variant on the target phenotype. Most variants will have no causal effect but fine-mapped variants within a credible set will have non-zero values and therefore non-zero values of $p_j$;

$\hat{\beta}_i$ is the residual effect size of variant i, i.e. the marginal effect of variant i, but with the effect of correlated variants in the credible set subtracted.

With these notations, and after normalising the effect sizes $\beta_i$ such that their variances are equal, we can perform the subtraction:

$$\hat{\beta}_i = \beta_i - \sum_j p_j r_{ij} \tilde{\beta}_j$$

where $r_{ij}$ captures the correlation between variants i and j, which is population specific and often referred to as the pattern of linkage disequilibrium. This subtraction is performed over all variants for which the fine-mapping probability $p_j$ is non-zero. Thereby, in this embodiment the step of subtracting the effect on the target phenotype of the set of fine-mapped variants from the input data comprises subtracting a weighted sum of effect sizes from the estimated effect size of each of the plurality of genetic variants on the target phenotype to obtain a residual effect size for each of the plurality of genetic variants. In this embodiment, the residual association data comprises the residual effect sizes.

The machine learning step of the estimation can then be performed on these residual effect sizes, in an identical manner to the way in which it would be performed if there was no fine-mapping (i.e. if steps S2 and S3 were not performed and the machine learning step operated directly on the input data). The addition of the fine-mapping can result in substantial differences in the output of the machine learning process. These substantial differences can be seen for example where the output from the machine learning algorithm is used to calculate PRS weights (defined below), as illustrated by the differences seen between FIG. 6 (showing PRS weights derived using a method with fine-mapping) and FIG. 7 (showing PRS weights derived using a method without fine-mapping). Furthermore, fine-mapped signals will approximate the true causal variant, which is generally shared across populations, thus leading to better robustness to population differences.

The machine learning step S5 may output a set of weights for non-fine-mapped variants (i.e. variants that were included in the input data 2 but which were not identified as fine-mapped variants in step S2) that indicate the significance assigned to the variants based on the residual signal, while accounting for the correlation between the variants. This process is significantly impacted by population specific correlation pattern between variants, resulting in sets of variants and weights that are population specific. Therefore, in an embodiment where the input data are derived from a plurality of different populations of the organism, the correlation $r_{ij}$ between the $i^{th}$ and $j^{th}$ variant is population-dependent.

FIGS. 6 and 7 show how the machine learning/LDpred weights are broadly distributed across the region, in contrast with the fine-mapping output that precisely characterises the variants inferred to be causal, or at least closely correlated to the true causal variant.

Incorporation of Related Trait Association Data in Variant Specific Priors

Bayesian machine learning algorithms for genetic prediction such as LDpred usually rely on a prior value that captures the probability that a variant is causal. Typically, the same prior value is assigned to all variants. This is referred to as a flat prior. Low prior values assigned to all variants lead to sparse models, with most weights small or equal to zero, while higher values lead to more diffuse models where the prediction weights are spread across a larger number of variants. An alternative to the standard LDpred model, which assumes a flat prior for each variant, is to leverage cross-trait information in order to adapt the prior probabilities in a variant specific manner.

One possible way to achieve this is to use logistic regression models; the binary outcome variable denotes the consistency of the direction of the marginal variant effect size between a well powered GWAS for the target phenotype and a GWAS for the same target phenotype using an independent cohort of individuals.

This means that where the input data are derived from a plurality of different genetic studies, the step of applying a machine learning algorithm to the residual association data may comprise using a prior probability for each of the plurality of genetic variants of being causal for the target phenotype that is dependent on the consistency of the strength of association between each genetic variant and the target phenotype between the different genetic studies. Strengths of association (e.g. P-values) from GWAS conducted on related traits are used as the input/predictive variables. The resulting linear combination of regression coefficients (where each regression coefficient captures how predictive the related trait is of the target phenotype) weighted by the input variables (i.e. the fitted values), followed by a normalisation procedure can then act as variant specific priors. As a result, the machine learning algorithm will generate higher weights for those variants with evidence of association at traits that are most related to the target phenotype.

Another option for the definition of variant specific weights is the incorporation of genomic annotations, derived from external genomic studies that are not GWAS. In such cases, the step of applying a machine learning algorithm to the residual association data comprises using a prior probability for each of the plurality of genetic variants of being causal for the target phenotype that is dependent on genomic annotations of the plurality of genetic variants in the region of interest. Such functional information, for example the presence of protein coding variants, or DNA binding sites for relevant transcription factors, can be combined with priors defined from GWAS data, in order to further enhance the machine learning algorithm and improve prediction performances.

Steps S6 and S7: Calculating PRS Model and PRSs

In an embodiment, the method further comprises calculating a PRS for an individual for the target phenotype using the fine-mapping predictive model (calculated in step S3) and the further predictive correlations identified by the machine learning algorithm (in step S5). In an embodiment, the fine-mapping predictive model and the further predictive correlations identified by the machine learning algorithm are used to define a PRS model (step S6). The PRS model can be used to calculate a PRS for an individual (step S7) given genetic data 3 from the individual. In an embodiment, the PRS model is a weighted sum over variants, where the weights are provided by the fine-mapping predictive model and the further predictive correlations identified by the machine learning algorithm. In an embodiment, the PRS is calculated as follows:

$$PRS = \sum_{l=1}^{L} \alpha_l x_l$$

where L is the number of variants that contribute to the PRS, each variant being included either in the fine-mapping predictive model or in the further predictive correlations from the machine learning algorithm, $x_l$ is the genotype for variant l, and $\alpha_l$ is the PRS weight, which quantifies the predictive impact of variant l on the target phenotype (i.e. quantifying the strength of association of variant l on the target phenotype). The PRS weights are related to effect sizes and may be specified by the fine-mapping predictive model (as calculated in step S3) or by the further predictive correlations from the machine learning algorithm (obtained in step S5).

For fine-mapped variants, the PRS weight $\alpha_l$ usually directly relates to the effect size of variant $\beta_l$ on the target phenotype, weighted by the probability $p_l$ that the variant is causal, hence:

$$\alpha_l = p_l \beta_l.$$

If an instrument trait was used, and a relationship has been established between the effect sizes for the instrument and target (such as a proportional $\beta_l = K \beta_l'$, where $\beta_l'$ is the effect size for the instrument study), the PRS weight is based on this instrument:

$$\alpha_l = p_l K \beta_l'.$$

For variants with PRS weights assigned by the machine learning algorithm, the relationship between the effect sizes and PRS weights may be less direct and depends on the specifics of the algorithm.

In some embodiments, the polygenic risk score for the individual may be derived from a combination (e.g. a sum) of a first partial polygenic risk score provided by applying the fine-mapping predictive model to genetic data from the individual (e.g. based on the fine-mapped variants in the genetic data only) and a second partial polygenic risk score provided by applying the further predictive correlations from the machine learning algorithm to the genetic data from the individual (e.g. based on variants in the genetic data other than the fine-mapped variants).

Machine learning steps leading to computation of PRS weights may be population specific, meaning that different PRSs can be applied to different individuals based on their ancestry, which can be identified using genetic data.

In some embodiments, the input data 2 are derived from a plurality of different populations of the organism (e.g. different classes of ancestry), and either or both of the following is satisfied:

i) the calculating of the fine-mapping predictive model is performed separately for portions of the input data corresponding to different populations to obtain multiple respective population-matched fine-mapping predictive models; and ii) the applying of the machine learning algorithm to the residual association data is performed separately for portions of the input data corresponding to different populations to obtain multiple respective sets of population-matched further predictive correlations.

A PRS for an individual from one of the populations (e.g. an individual having genes that are predominantly from one of the different populations) may be calculated as follows. Input data is received from the individual. A PRS is calculated for the individual by performing either or both of:

i) applying a population-matched fine-mapping predictive model to all of the input data from the individual, the population-matched fine-mapping predictive model being matched to the population of the individual; and ii) applying a set of population-matched further predictive correlations to all of the input data from the individual, the set of population-matched further predictive correlations being matched to the population of the individual.

Alternative Implementation for Calculating the PRS for Admixed Individuals

For individuals who are a mixture of two or more well defined ancestry groups, such as African-American individuals, different segments of chromosomes can be assigned to each of these ancestries. A key motivation for the fine-mapping approach is to identify causal variants and CS that are more likely to be consistent across populations. However, beyond fine-mapping, the class of predictive algorithms, which encompass machine learning methodologies, are dependent on the pattern of linkage disequilibrium, and therefore on the target population. Consequently, different PRSs will be derived for different populations.

The field of population genetics has established methodologies to match chromosome segments of an individual to the distinct populations from which these segments originate. This process is referred to as "chromosome painting". To properly handle admixed individuals, we apply this chromosome painting step to the genotype data of the individual in question. Rather than assigning an individual to a single population, we construct an admixed PRS that applies the relevant, population specific, PRS to the appropriate chromosome segment, considering maternal and paternal chromosome copies separately.

In an embodiment of this type, input data from the individual (having genes from a mixture of the different populations) is received. A PRS is calculated for the individual by performing either or both of:

i) matching each of multiple population-matched fine-mapping predictive models to a corresponding portion of the input data that matches the population of the population-matched fine-mapping predictive model and applying each matched fine-mapping predictive model to the corresponding portion of the input data; and ii) matching each of multiple sets of population-matched further predictive correlations to a corresponding portion of the input data that matches the population of the set of population-matched further predictive correlations and applying each matched set of further predictive correlations to the corresponding portion of the input data.

In practice, the fine-mapping predictive model is expected to be mostly consistent across populations, such that the set of fine-mapped variants, and even in some cases the effect sizes of the fine-mapped variants, will be unique, with cross population information being used to get them right. Thus, in the above methods, it is expected that it would of most value to perform the matching to populations with respect to the sets of further predictive correlations. Thus, in an embodiment the fine-mapping predictive model is established by combining data from the plurality of available population datasets, for either or both of: i) the choice of fine-mapped variants and ii) the effect sizes associated with these variants. In such embodiments, a polygenic risk score may be derived by applying a shared population-consistent fine-mapping predictive model (i.e. a fine-mapping predictive model that is valid for multiple individuals regardless of which population or populations they belong to) to input data from the individual, with only the further predictive correlations being established in a population specific manner.

The invention claimed is:

1. A computer-implemented method of analysing genetic data about an organism to obtain information about the organism, the method comprising:

receiving input data comprising strengths of association between one or more phenotypes including a target phenotype and a plurality of genetic variants in a region of interest of the genome of the organism;

applying a fine-mapping algorithm to all or a subset of the input data to identify one or more independent phenotype-variant associations within the region of interest, comprising identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one;

generating, on the basis of the input data and the set of one or more fine-mapped variants, a fine-mapping predictive model quantifying an effect on the target phenotype of the set of one or more fine-mapped variants;

subtracting from the input data, using the fine-mapping predictive model, the effect on the target phenotype of the set of one or more fine-mapped variants to obtain residual association data, wherein the subtracting comprises subtracting a weighted sum of effect sizes from an estimated effect size of each of the plurality of genetic variants on the target phenotype to obtain a residual effect size for each of the plurality of genetic variants, and wherein the residual association data comprises the residual effect size for each of the plurality of genetic variants;

inputting, into a machine learning algorithm, at least the residual association data;

outputting, by the machine learning algorithm, predicted weight values for non-fine mapped variants, wherein the predicted weight values indicate a significance assigned to the non-fine mapped variants based on residual signals, while accounting for correlation between the non-fine mapped variants, wherein the non-fine mapped variants are variants included in the plurality of genetic variants but are not identified by the fine-mapping algorithm as the one or more fine-mapped variants, and wherein the outputting comprises iterating through multiple selections of variants from the plurality of genetic variants and, as the variants are selected, estimating the residual signal for each of the variants based on the residual association data;

generating a polygenic risk score model based on the fine-mapping predictive model and the predicted weight values for the non-fine mapped variants; and applying the polygenic risk score model to genetic data from an individual to determine a polygenic risk score for the individual for the target phenotype.

2. The method of claim 1, wherein the strengths of association comprise an estimated effect size of each of the plurality of genetic variants on the target phenotype, and a standard error of each of the estimated effect sizes.

3. The method of claim 1, wherein the step of receiving input data comprises:

receiving individual level data comprising genotypes and corresponding phenotypes for each of a plurality of individuals; and determining using the individual level data an estimated effect size of each of the plurality of genetic variants on the target phenotype and a standard error of each of the estimated effect sizes.

4. The method of claim 1, wherein the identifying of the set of one or more fine-mapped variants is performed using an iterative method, wherein each iteration comprises:

identifying, on the basis of the input data, a fine-mapped variant within the region of the genome different from any previously identified fine-mapped variant;

updating the input data to account for the effect on the target phenotype of the fine-mapped variants already identified, using a matrix of correlations between the genetic variants within the region of the genome; and determining whether to perform a further iteration on the basis of the updated input data.

5. The method of claim 1, wherein the identifying of the set of one or more fine-mapped variants comprises using a plurality of instrument traits known to affect the target phenotype, the use of the instrument traits comprising:

determining an initial set of fine-mapped variants for the instrument traits; and determining whether to include each fine-mapped variant of the initial set of fine-mapped variants for the instrument traits in the set of one or more fine-mapped variants for the target phenotype on the basis of a relationship between the plurality of instrument traits and the target phenotype.

6. The method of claim 5, wherein the generating of the fine-mapping predictive model comprises:

determining effect sizes on the one or more instrument traits of the initial set of fine-mapped variants for the one or more directly causal instrument traits, and determining an effect size for the target phenotype of each fine-mapped variant of the initial set of fine-mapped variants for the instrument traits included in the set of one or more fine-mapped variants for the target phenotype on the basis of a predetermined relationship between effect sizes for the instrument traits and effect sizes for the target phenotype.

7. The method of claim 1, wherein the identifying of the set of one or more fine-mapped variants comprises identifying an initial set of fine-mapped variants for one or more directly causal instrument traits known to affect the target phenotype.

8. The method of claim 1, wherein:

the strengths of association comprise an estimated effect size of each of the plurality of genetic variants on the target phenotype, and a standard error of each of the estimated effect sizes; and the fine-mapping predictive model comprises a fine-mapped effect size on the target phenotype for each of the fine-mapped variants, the fine-mapped effect size being calculated from the estimated effect size of the fine-mapped variants taking account of the estimated probability of the fine-mapped variants being causal for the phenotype-variant association.

9. The method of claim 1, wherein the effect on the target phenotype of the set of one or more fine-mapped variants is inferred using a machine learning algorithm.

10. The method of claim 9, wherein the set of one or more fine-mapped variants further comprises one or more variants known to have a high likelihood of being causal for the target phenotype.

11. The method of claim 1, wherein:

the strengths of association comprise an estimated effect size of each of the plurality of genetic variants on the target phenotype, and a standard error of each of the estimated effect sizes; and the step of subtracting from the input data the effect on the target phenotype of the set of one or more fine-mapped variants comprises obtaining the residual effect size for each of a plurality of the genetic variants in the input data, the residual association data comprising the residual effect sizes, wherein, after appropriate renormalisation of the effect sizes to ensure equal variance, the residual effect size $\hat{\beta}_i$ for genetic variant i is given by:

$$\hat{\beta}_i = \beta_i - \sum_{j=1}^{N} p_j r_{ij} \hat{\beta}_j$$

where $\beta_i$ is the estimated marginal effect size of genetic variant i, N is the number of fine-mapped variants, $p_j$ is the probability that variant j is causal, $\hat{\beta}j$ is the fine-mapped effect size of the $j^{th}$ fine-mapped variant on the target phenotype, and $r_{ij}$ is a correlation between the $j^{th}$ fine-mapped variant and genetic variant i.

12. The method of claim 1, wherein the input data are derived from a plurality of different genetic studies, and the step of inputting into the machine learning algorithm comprises using a prior probability for each of the plurality of genetic variants of being causal for the target phenotype that is dependent on the consistency of the strength of association between each genetic variant and the target phenotype between the different genetic studies.

13. The method of claim 1, wherein the step of inputting into the machine learning algorithm comprises using a prior probability for each of the plurality of genetic variants of being causal for the target phenotype that is dependent on genomic annotations of the plurality of genetic variants in the region of interest.

14. The method of claim 1, wherein the step of applying the polygenic risk score model to genetic data from the individual further comprises applying the fine-mapping predictive model and the non-fine mapped variants identified by the machine learning algorithm.

15. The method of claim 14, wherein the polygenic risk score is given by the followed weighted sum:

$$PRS = \sum_{l=1}^{L} \alpha_l x_l$$

where L is the number of variants that contribute to the PRS, each variant being included either in the fine-mapping predictive model or in the non-fine mapped variants from the machine learning algorithm, $\alpha_l$ quantifies a strength of association of variant l on the target phenotype, the strength of association being specified by the fine-mapping predictive model or by the non-fine mapped variants from the machine learning algorithm, and $x_l$ is the genotype for variant l.

16. The method of claim 14, wherein the polygenic risk score for the individual is derived from a combination of a first partial polygenic risk score provided by applying the fine-mapping predictive model to genetic data from the individual and a second partial polygenic risk score provided by applying the non-fine mapped variants of the machine learning algorithm to the genetic data from the individual.

17. The method of claim 1, wherein the input data are derived from a plurality of different populations of the organism, and either or both of the following is satisfied:

the generating of the fine-mapping predictive model is performed separately for portions of the input data corresponding to different populations to obtain multiple respective population-matched fine-mapping predictive models; and the inputting into the machine learning algorithm at least the residual association data is performed separately for portions of the input data corresponding to different populations to obtain multiple respective sets of population-matched further predictive correlations.

18. The method of claim 17, further comprising:

receiving input data from an individual having genes from a mixture of the different populations; and generating a polygenic risk score for the individual by performing either or both of:

matching each of multiple population-matched fine-mapping predictive models to a corresponding portion of the input data that matches the population of the population-matched fine-mapping predictive model and applying each matched fine-mapping predictive model to the corresponding portion of the input data; and matching each of multiple sets of population-matched further predictive correlations to a corresponding portion of the input data that matches the population of the set of population-matched further predictive correlations and applying each population-matched set of further predictive correlations to the corresponding portion of the input data.

19. The method of claim 18, wherein the matching of each of multiple sets of population-matched further predictive correlations is performed and the matching of each of multiple population-matched fine-mapping predictive models is not performed, the generation of the polygenic risk score further comprising applying a shared population-consistent fine-mapping predictive model to the input data from the individual.

20. The method of claim 17, further comprising:

receiving input data from an individual having genes predominantly from one of the different populations; and generating a polygenic risk score for the individual by performing either or both of:

applying a population-matched fine-mapping predictive model to all of the input data from the individual, the population-matched fine-mapping predictive model being matched to the population of the individual; and applying a set of population-matched further predictive correlations to all of the input data from the individual, the set of population-matched further predictive correlations being matched to the population of the individual.

21. The method of claim 20, wherein the applying of the set of population-matched further predictive correlations is performed and the applying of the population-matched fine-mapping predictive model is not performed, the calculation of the polygenic risk score comprising applying a shared population-consistent fine-mapping predictive model to the input data from the individual.

22. The method of claim 1, wherein the identifying of the set of one or more fine-mapped variants by the fine-mapping algorithm takes account of associations between the plurality of genetic variants and phenotypes other than the target phenotype.

23. The method of claim 1, wherein the organism is a human.

24. An apparatus comprising:

one or more processors; and one or more computer-readable media storing instructions which, when executed by the one or more processors, cause units of the apparatus to perform operations, the units comprising:

a receiving unit configured to receive input data comprising strengths of association between one or more phenotypes including a target phenotype and a plurality of genetic variants in a region of interest of the genome of the organism; and a data processing unit configured to:

apply a fine-mapping algorithm to all or a subset of the input data to identify one or more independent phenotype-variant associations within the region of interest, by identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one;

generate, on the basis of the input data and the set of one or more fine-mapped variants, a fine-mapping predictive model quantifying an effect on the target phenotype of the set of one or more fine-mapped variants;

subtract, using the fine-mapping predictive model, the effect on the target phenotype of the set of one or more fine-mapped variants to obtain residual association data, wherein the subtracting comprises subtracting a weighted sum of effect sizes from an estimated effect size of each of the plurality of genetic variants on the target phenotype to obtain a residual effect size for each of the plurality of genetic variants, and wherein the residual association data comprises the residual effect size for each of the plurality of genetic variants;

input, into a machine learning algorithm, at least the residual association data;

output, by the machine learning algorithm, predicted weight values for non-fine mapped variants, wherein the predicted weight values indicate a significance assigned to the non-fine mapped variants based on residual signals, while accounting for correlation between the non-fine mapped variants, wherein the non-fine mapped variants are variants included in the plurality of genetic variants but are not identified by the fine-mapping algorithm as the one or more fine-mapped variants, and wherein the outputting comprises iterating through multiple selections of variants from the plurality of genetic variants and, as the variants are selected, estimating the residual signal for each of the variants based on the residual association data;

generate a polygenic risk score model based on the fine-mapping predictive model and the predicted weight values for the non-fine mapped variants; and apply the polygenic risk score model to genetic data from an individual to determine a polygenic risk score for the individual for the target phenotype.

25. A system comprising:

one or more processors; and one or more computer-readable media storing instructions which, when executed by the one or more processors, cause the system to perform operations comprising:

receiving input data comprising strengths of association between one or more phenotypes including a target phenotype and a plurality of genetic variants in a region of interest of the genome of the organism;

applying a fine-mapping algorithm to all or a subset of the input data to identify one or more independent phenotype-variant associations within the region of interest, comprising identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one;

generating, on the basis of the input data and the set of one or more fine-mapped variants, a fine-mapping predictive model quantifying an effect on the target phenotype of the set of one or more fine-mapped variants;

subtracting from the input data, using the fine-mapping predictive model, the effect on the target phenotype of the set of one or more fine-mapped variants to obtain residual association data, wherein the subtracting comprises subtracting a weighted sum of effect sizes from an estimated effect size of each of the plurality of genetic variants on the target phenotype to obtain a residual effect size for each of the plurality of genetic variants, and wherein the residual association data comprises the residual effect size for each of the plurality of genetic variants;

inputting, into a machine learning algorithm, at least the residual association data;

outputting, by the machine learning algorithm, predicted weight values for non-fine mapped variants, wherein the predicted weight values indicate a significance assigned to the non-fine mapped variants based on residual signals, while accounting for correlation between the non-fine mapped variants, wherein the non-fine mapped variants are variants included in the plurality of genetic variants but are not identified by the fine-mapping algorithm as the one or more fine-mapped variants, and wherein the outputting comprises iterating through multiple selections of variants from the plurality of genetic variants and, as the variants are selected, estimating the residual signal for each of the variants based on the residual association data;

generating a polygenic risk score model based on the fine-mapping predictive model and the predicted weight values for the non-fine mapped variants; and applying the polygenic risk score model to genetic data from an individual to determine a polygenic risk score for the individual for the target phenotype.

26. One or more non-transitory computer-readable media storing instructions which, when executed by one or more processors, cause a system to perform operations comprising:

receiving input data comprising strengths of association between one or more phenotypes including a target phenotype and a plurality of genetic variants in a region of interest of the genome of the organism;

applying a fine-mapping algorithm to all or a subset of the input data to identify one or more independent phenotype-variant associations within the region of interest, comprising identifying for each association a set of one or more fine-mapped variants from the plurality of genetic variants, and determining for each fine-mapped variant an estimated probability of being causal for the phenotype-variant association, the sum of the probabilities for the fine-mapped variants within the set adding to one;

generating, on the basis of the input data and the set of one or more fine-mapped variants, a fine-mapping predictive model quantifying an effect on the target phenotype of the set of one or more fine-mapped variants;

subtracting from the input data, using the fine-mapping predictive model, the effect on the target phenotype of the set of one or more fine-mapped variants to obtain residual association data, wherein the subtracting comprises subtracting a weighted sum of effect sizes from an estimated effect size of each of the plurality of genetic variants on the target phenotype to obtain a residual effect size for each of the plurality of genetic variants, and wherein the residual association data comprises the residual effect size for each of the plurality of genetic variants;

inputting, into a machine learning algorithm, at least the residual association data;

outputting, by the machine learning algorithm, predicted weight values for non-fine mapped variants, wherein the predicted weight values indicate a significance assigned to the non-fine mapped variants based on residual signals, while accounting for correlation between the non-fine mapped variants, wherein the non-fine mapped variants are variants included in the plurality of genetic variants but are not identified by the fine-mapping algorithm as the one or more fine-mapped variants, and wherein the outputting comprises iterating through multiple selections of variants from the plurality of genetic variants and, as the variants are selected, estimating the residual signal for each of the variants based on the residual association data;

generating a polygenic risk score model based on the fine-mapping predictive model and the predicted weight values for the non-fine mapped variants; and applying the polygenic risk score model to genetic data from an individual to determine a polygenic risk score for the individual for the target phenotype.

* * * * *